US007846861B2

(12) United States Patent
Redlingshöfer et al.

(10) Patent No.: US 7,846,861 B2
(45) Date of Patent: Dec. 7, 2010

(54) PROCESS FOR REGENERATING A CATALYST

(75) Inventors: Hubert Redlingshöfer, Münchsteinach (DE); Christoph Weckbecker, Gründau-Lieblos (DE); Klaus Huthmacher, Geinhausen (DE); Andreas Dörflein, Großkrotzenburg (DE)

(73) Assignee: Evonik Degussa GmbH, Essen (DE)

( * ) Notice: Subject to any disclaimer, the term of this patent is extended or adjusted under 35 U.S.C. 154(b) by 563 days.

(21) Appl. No.: 12/017,911

(22) Filed: Jan. 22, 2008

(65) Prior Publication Data

US 2008/0214384 A1    Sep. 4, 2008

(30) Foreign Application Priority Data

Jan. 29, 2007    (DE) .................. 10 2007 004 350

(51) Int. Cl.
*B01J 38/46*    (2006.01)
(52) U.S. Cl. ........................ 502/36; 502/514; 502/515
(58) Field of Classification Search ............... 502/36, 502/56, 515, 514
See application file for complete search history.

(56) References Cited

U.S. PATENT DOCUMENTS 5,387,720 A    2/1995    Neher 5,608,133 A    3/1997    Change
2006/0091045 A1    5/2006    Figueras

FOREIGN PATENT DOCUMENTS

| DE | 42 38 492 A2 | 11/1992 |
| DE | 42 38 493 C1 | 11/1992 |
| EP | 417 723 A2 | 9/1990 |
| EP | 0 598 229 A1 | 10/1993 |
| EP | 0 598 229 A | 3/1994 |
| WO | 2006 087083 A | 8/2006 |
| WO | 2006/087083 A2 | 8/2006 |
| WO | 2006/087084 A2 | 8/2006 |

OTHER PUBLICATIONS

Ullmann's Encyclopedia of Industrial Chemistry, 6th edition, 1999; "Acrolein and Methacrolein" pp. 1-24.
Organic Syntheses, Coll. vol. I, p. 15-18 (1941; vol. 6, p. 1 (1926).
Dao, Le H. et al., ACS symp. Ser.: 376; Reactions of Model Compounds of Biomass-Pyrolysis Oils over ZSM-5 Zeolite Catalysts, Chapter 27, pp. 328-341.
Studies in Surface Science and Catalysts, vol. 51, 1989: "New Solid Acids and Bases, Their Catalytic Properties" by K. Tanabe et al., Chapter 2, pp. 5-9; Chapter 1, pp. 1-3 .
International Search Report.
Ullmann's Encyclopedia of Industrial Chemistry, 6th edition, 1999.
Organic Synthesis I, 15-18 (1964).
Dao, Le H. et al., ACS symp. Ser.: 376 (Pyrolysis Oils Biomass) 328-341.

*Primary Examiner*—Edward M Johnson
(74) *Attorney, Agent, or Firm*—Smith, Gambrell & Russell, LLP

(57) ABSTRACT

A process for regenerating a catalyst used in the preparation of acrolein from glycerol, which comprises tungsten compounds and has acidic properties and at least one promoter.

14 Claims, No Drawings

PROCESS FOR REGENERATING A CATALYST

INTRODUCTION AND BACKGROUND

The invention relates to the processes for regenerating a catalyst used in the preparation of acrolein from glycerol which comprises tungsten compounds and has acidic properties and at least one promoter.

Acrolein is an important intermediate and is of great economic significance for the preparation of acrylic acid, D,L-methionine and the methionine hydroxy analogue 2-hydroxy-4-methylthiobutyric acid (MHA). Methionine is an essential amino acid which is used, inter alia, as a supplement in feeds. Nutrition-improving feed additives are nowadays an indispensable constituent in animal nutrition. They serve for better utilization of the food supply, stimulate growth and promote protein formation. One of the most important of these additives is the essential amino acid methionine, which assumes a prominent position as a feed additive in poultry breeding in particular. In this field, though, methionine replacements such as methionine hydroxy analogue (abbreviated to MHA) also have not inconsiderable significance, since they have similar growth-stimulating properties to the amino acid known for this purpose. Acrylic acid is an important starting material for preparing polymers which, for example owing to their water absorption capacity, are used as superabsorbents.

According to the prior art, acrolein is synthesized by heterogeneously catalysed selective oxidation of propene over mixed oxide catalysts. EP 417723 describes the synthesis over complex mixed multimetal oxide catalysts at temperatures of 300 to 380° C. and pressures of 1.4 to 2.2 bar. Ullmann's Encyclopedia of Industrial Chemistry, 6th edition, 1999 describes the overall process including workup, in which several by-products are removed. Once the reactant mixture of propene, air and water has been converted at least partly over the catalyst, quenching is first effected to remove high-boiling by-products such as polymers, acrylic acid and acetic acid. In the downstream absorber, acrolein is washed out. After the desorption, the absorbent is recovered by purifying the crude acrolein obtained by distillation in several stages.

It is known that glycerol can be dehydrated in the presence of acidic substances to various products. According to Organic Synthesis I, 15-18 (1964), treatment of a mixture of pulverulent potassium hydrogensulphate, potassium sulphate and glycerol at 190 to 200° C. affords acrolein in a yield of between 33 and 48%. Owing to the low yields and the high salt burdens, this process is, however, not suitable for the industrial scale.

In the course of studies of model substances of biomass pyrolysis oils, the catalytic treatment of glycerol over H-ZSM5 zeolites at 350 to 500° C. has also been studied—see Dao, Le H. et al. ACS Symp. Ser.:376 (Pyrolysis Oils Biomass) 328-341 (1988). Hydrocarbons are formed only in low yields.

Moreover, EP 0598229, U.S. Pat. No. 5,387,720 describe the acid-catalysed conversion of glycerol to acrolein in the gas phase and in the liquid phase. In this case, it is solely the acid strength (Hammett acid function) that determines suitability as a catalyst. DE 42 38 492 relates to the synthesis of 1,2- and 1,3-propanediol by dehydrating glycerol with high yields.

WO 2006/087083 discloses a process for preparing acrolein from glycerol over acidic catalysts, in which oxygen is added to the reaction mixture.

A similar process is described in WO 2006/087084. The catalysts used there have a Hammett acidity H0 in the range of −9 to −18.

The catalysts used in chemical technology are subject virtually without exception to deactivation, such that the catalyst has to be exchanged at periodic intervals in order to maintain an economic space-time yield. The lifetime of the catalysts is very different depending on the reaction system and may be a few hours up to many years. A periodic regeneration of the catalyst counteracts the deactivation at least partly and again significantly increases the activity of the catalyst. This is used industrially frequently in syntheses when carbon-containing deposits form on the catalyst, which cover the active sites. According to the reaction system, these deposits are different. As a result of the inventive selection of the catalyst and the addition of promoters which improve the regeneratability, it is possible to improve the space-time yield in the dehydration of glycerol.

It is an object of the invention to provide a The process for regenerating a catalyst which is suitable for the dehydration of glycerol, the catalyst having a relatively low carbonization tendency and being easy to regenerate.

It has been found that solid-state catalysts which comprise tungsten compounds and have a Hammett acidity Ho of <+2 and which comprise one or more promoters selected from compounds from the group of elements comprising, preferably consisting of, gold, silver, copper, vanadium, platinum, rhodium, palladium, ruthenium, samarium, cerium, scandium, yttrium, lanthanum, zinc, magnesium, iron, cobalt or nickel and optionally compounds of the elements lithium, sodium, potassium or caesium, and/or montmorillonite or acidic zeolites solve this problem.

The latter two compounds are present in the catalyst as promoters, optionally in an amount of 0.1 to 30% by weight, preferably 5 to 25% by weight.

Preference is given to catalysts which have a Hammett acidity $H_o$ of <+2 to −20.

Since glycerol is a reactive molecule which tends to form relatively high-boiling compounds at high temperatures by the reaction of two or more glycerol molecules with one another, the catalyst is carbonized by deposits of carbon-containing molecules on the surface. This leads to a reduction in activity.

To achieve a high space-time yield, it is not only the Hammett acid strength of the catalyst that is important, but also the regenerability and the tendency to carbonization.

DETAILED DESCRIPTION OF INVENTION

The catalyst used in accordance with the invention comprises at least one promoter which accelerates the regeneration of the catalyst. Lifetime and space-time yield likewise increase significantly, since deactivation by carbonization in particular is at least for the most part eliminated in the case of these catalysts, and the activity is significantly increased. The conversion of glycerol and the yield of acrolein can thus be maintained at a high level depending on the time. This is of great significance especially for an industrial implementation of the synthesis, since an exchange of the catalyst and associated plant shutdowns would cause high costs.

In addition to the Brønsted-acidic groups, it is also possible for hydroxyl groups or Lewis-acidic sites to influence the activity and selectivity. Equally, in addition to the promoters, the addition of compounds of one or more of the elements selected from the group comprising silicon, phosphorus, niobium, zinc, tin, magnesium, aluminium, molybdenum or vanadium or activated carbon to a catalyst comprising tungsten compounds can modify the surface of the catalyst or reduce the concentration of active sites, such that the yield is improved further. This especially reduces the formation of high boilers or coke precursors which are formed from two or more adjacent adsorbed glycerol molecules or intermediates and are adsorbed in a fixed manner.

Suitable solid-state catalysts are especially also the types known from U.S. Pat. No. 5,387,720 (EP 0 598 229 A1), when they comprise a tungsten compound and additionally one or more of the promoters mentioned. These catalysts are solid substances which are essentially insoluble in the reaction medium, have a mono- or polyphasic structure and have an $H_o$ of less than +2, preferably less than −3. The $H_o$ corresponds to the Hammett acid function and can be determined by the so-called amine titration using indicators or by adsorption of a gaseous base—see Studies in surface science and catalysis, Vol. 51, 1989: "New solid acids and bases, their catalytic properties" by K. Tanabe et al. chapter 2, especially pages 5-9. Chapter 1 (pages 1-3) of the aforementioned document mentions numerous solid acids from which the person skilled in the art, if appropriate after determining the $H_o$ value, can select the suitable catalyst for the inventive modification. Suitable base substances for the inventive dehydration catalysts are preferably (i) natural and synthetic silicatic substances, especially mordenite, acidic zeolites and activated carbon; (ii) support materials, such as oxidic or silicatic substances, for example $Al_2O_3$, $SiO_2$, $ZrO_2$, $TiO_2$; (iii) oxides and mixed oxides, for example gamma-$Al_2O_3$ and ZnO—$Al_2O_3$, $SiO_2$—$Al_2O_3$, $ZrO_2$—$SiO_2$, $ZrO_2$—$HfO_2$ mixed oxides or heteropolyacids.

Suitable compounds for providing the active tungsten sites may, for example, be ammonium tungstate, ammonium metatungstate, tungstic acid, tungstosilicic acid, tungstophosphoric acid or heteropolyacids with tungsten as a constituent. These compounds or mixtures thereof are then either used directly as the catalyst or used as catalyst precursors. In the case of addition of further elements, preference is given to a preceding mixing as a powder, in a solution or in a melt. In one embodiment of the invention, the catalytically active compounds are bound on a support.

The support materials used may, for example, be aluminium oxide, titanium dioxide, silicon dioxide, zirconium dioxide, activated carbon or mixtures thereof. The supports serve predominantly to increase the specific surface area or to fix the active sites.

The catalysts used in accordance with the invention are prepared by processes known to those skilled in the art. When the active components are applied to a support, this is preferably done by impregnating the support, for example by means of the incipient-wetness method by spraying. The active components may also be obtained by precipitation or extraction from a solution. Subsequently, the catalyst can then be shaped, if appropriate with addition of supports, adhesion promoters or pore formers, by pressing, extrusion, coating or agglomeration. The catalyst typically has a particle diameter between 0.04 mm and 20 mm, preferably between 0.1 and 10 mm, especially between 0.5 and 7 mm. The active compounds may also be applied in the form of a coating. When no support is used, preference is given to catalyst preparation by extrusion, pressing of tablets or buildup by agglomeration.

For the dehydration in the gas phase, particular preference is given to catalysts having an $H_o$ between −3 and −8.2. Suitable catalyst systems which comprise tungsten and promoters are, for example, $SiO_2/H_2WO_4$, $Pd/H_2WO_4$, $Pt/H_2WO_4$, $Pd/WO_x/ZrO_2$, $Cu/WO_x/ZrO_2$, $WO_x/SiO_2/ZrO_2$.

The process for preparing acrolein by dehydrating glycerol is performed in the presence of solid-state catalysts which comprise tungsten compounds and have a Hammett acidity $H_o$ of <+2 to preferably −20 and which comprise one or more promoters selected from compounds from the group of elements comprising, preferably consisting of, gold, silver, copper, vanadium, platinum, palladium, rhodium, ruthenium, samarium, cerium, yttrium, scandium, lanthanum, zinc, magnesium, iron, cobalt or nickel, or mixtures thereof. In addition compounds from the group of elements lithium, sodium, potassium or caesium and/or montmorillonite or acidic zeolites are optionally present.

The latter two compounds are present in the catalyst as promoters, optionally in an amount of 0.1 to 30% by weight, preferably 5 to 25% by weight.

The dehydration is effected preferably in the absence of oxygen. In one embodiment, also in the presence of hydrogen in an amount of 0.1 to 10% by volume, in particular of 0.5 to 5% by volume, based on the total amount of the reaction mixture. The dehydration is performed in the presence of the catalysts described above.

The concentration of the glycerol in the reaction mixture is preferably lowered by the addition of suitable gaseous compounds inert under the selected reaction conditions.

As a result, side reactions to give oligomers, polymers and other high boilers are minimized. The solvents and diluents known to those skilled in the art are used, for example water, nitrogen, air, carbon dioxide, methane and/or hydrogen, alcohols, for example methanol and ethanol, acetone, toluene or methyl isobutyl ketone. Preference is given to dilution media which, after the condensation, can be isolated from acrolein in a simple manner by phase separation.

In the reaction mixture, the glycerol concentration is between 1 and 100% by weight, preferably between 1 and 70% by weight and especially between 5 and 40% by weight.

One advantage of the Process consists in the fact that glycerol solutions having a content of 5 to 40% by weight are also usable. So-called crude glycerols without preceding concentration or purification can thus be used directly for the synthesis of acrolein.

The reaction is performed at a temperature between 150 and 450° C., preferably between 180 and 350° C., more preferably between 220 and 320° C. Typically, the pressure is between 0.1 and 200 bar, preferably between 0.5 and 50 bar, more preferably between 0.9 and 10 bar.

The process can be performed in the liquid phase or in the gas phase. In both embodiments, the same acidic solid-state catalysts can be used in principle, but it has been found that particular catalysts are preferably suitable for dehydration in the gas phase and others preferably for that in the liquid phase.

The reaction in the gas phase is particularly preferred because the glycerol conversion is virtually complete (>95%) and the gaseous reaction mixture leaving the catalyst can be condensed or absorbed directly to obtain an aqueous acrolein solution which additionally comprises by-products which have been formed; this condensate can in many cases be processed further directly. The partial condensation and/or absorption of the reaction mixture can be effected in several stages. If desired, acrolein can be obtained from the reaction mixture, if appropriate together with a portion of the water, by fractional condensation, absorption, desorption and subsequent distillation.

A portion of the water is circulated, in the course of which it is evaporated and condensed with utilization of thermal integration.

An inert gas or a diluent can also be circulated.

In the case of reaction in the liquid phase, it is appropriate to perform the dehydrogenation only up to a glycerol conversion of about 15 to 25%, since the selectivity decreases when the conversion is increased. After the stated conversion has been attained, acrolein formed is removed from the reaction mixture alone or together with a portion of the water in a known manner, typically by distillation or by $N_2$ stripping. The acrolein can be isolated by condensation or scrubbing with water. The glycerol-containing reaction mixture freed of acrolein is recycled into the dehydration stage. One advantage of dehydration in the liquid phase over that in the gas phase consists in the lower energy demand, because only the acrolein removed from the reaction mixture and a portion of water which is distilled over with it have to be evaporated.

The dehydration in the gas phase is effected preferably within the temperature range between 240 and 320° C., that in the liquid phase preferably between 250 and 300° C. In the case of liquid phase dehydration, the apparatus is subjected to at least such a pressure which is sufficient to maintain the liquid phase.

The dehydration is effected in a fixed bed reactor, a fluidized bed reactor, in a reactor with a circulating fluidized bed, a moving bed reactor or a reactor with regenerator-riser (-downer) design. It can be performed continuously or batchwise.

Moreover, the combination of the reaction with reactant workup or product workup by means of a reactive distillation is possible and advisable, since the boiling point differences between glycerol and acrolein are very large. In this case, the catalyst is positioned either in the bottom and/or in the column part. The catalyst introduced may, for example, be present in the form of a bed, suspension or a coating. A further advantage of the reactive distillation consists in the fact that high-boiling impurities are discharged from crude glycerol at the bottom of the column with further high boilers which can be formed as by-products. Acrolein and low boilers are then removed via the top.

Acrolein formed can also be removed from the reaction mixture in a known manner, alone or together with a portion of the solution or dilution medium, by stripping, distillation or extraction. Unconverted glycerol can then be recycled into the reaction stage.

The catalyst used in accordance with the invention is also notable for good regeneratability.

The invention provides a process for regenerating solid-state catalysts which comprise tungsten and have a Hammett acidity $H_o$ of <+2 to preferably −20, and which comprise one or more promoters selected from compounds from the group of elements comprising, preferably consisting of, gold, silver, copper, vanadium, platinum, palladium, rhodium, ruthenium, samarium, cerium, yttrium, lanthanum, zinc, magnesium, rhodium, iron, cobalt or nickel or mixtures thereof, optionally additionally compounds of the elements lithium, sodium, potassium or caesium, and/or montmorillonite or acidic zeolites, which, after use in a process for dehydrating glycerol to acrolein, have a lower activity and/or selectivity than before this use, in which the catalysts are exposed to an oxidizing or reducing atmosphere for the regeneration, without reactants from the glycerol dehydration being present.

Depending on their standard potential, individual elements, after the regeneration of the catalyst under reducing conditions, may also be present in metallic form on the catalyst.

The tungsten-containing compounds are selected from the group of ammonium tungstate, tungstophosphoric acid, tungstic acid, tungstosilicic acid, tungsten oxides or heterophosphoric acids with tungsten as the constituent. Particularly suitable examples are $Pd/H_2WO4$, $Pt/H2WO_4$, $PdWO_x/ZrO_2$, $Ce/WO_x/ZrO_2$.

The catalysts preferably comprise natural or synthetic silicatic or oxidic compounds as supports.

Also suitable are catalysts which comprise support materials modified with mono-, di- or polybasic inorganic acids or salts of inorganic salts.

Preference is also given to catalysts which comprise, as support materials, aluminium oxide, titanium dioxide, silicon dioxide, zirconium dioxide, activated carbon or mixtures thereof.

The regeneration can be effected either under oxidation conditions or under hydrogenation conditions. In both cases, the coke which has formed on the surface of the catalyst by deposition of hydrocarbons during the reaction is removed completely or partly. The suitable promoters which are part of the catalyst are, in the case of regeneration by oxidation, generally components which accelerate the conversion of hydrocarbons to carbon oxides, for example gold, silver, copper, vanadium or platinum, optionally in metallic form; when the regeneration is performed under hydrogenating conditions, promoters with strongly hydrogenating action are added to the acidic catalyst, for example cobalt, nickel, palladium, platinum or rhodium.

The regeneration is effected separately from the conversion of glycerol, either in time or in location. In the case of time separation, the feeding of glycerol into the reactor is stopped and then the regeneration is performed before the reactant mixture is fed in again. This operation is then repeated periodically as often as desired. For the performance of this regeneration method, suitable arrangements are especially the cyclic operation of 2 or more fixed bed reactors in order to be able to obtain a continuous product stream. In this case, one of the reactors is regenerated while at least one of the reactors is used for the production of acrolein. The time intervals for reaction and regeneration can be selected as desired. Preference is given to the uninterrupted production of acrolein within a time interval of 2 to 3000 h, especially 4 to 400 h, before the catalyst is regenerated within a time interval of 0.5 to 100 h, especially 1 to 10 h.

When the regeneration is effected at a separate location, the catalyst is moved continuously between preferably 2 reactors. In one of the reactors, the glycerol conversion to acrolein takes place continuously. In the other reactor, the catalyst is regenerated continuously. Suitable reactor designs are the moving bed reactor or the regenerator-riser (-downer) design. The moving bed is notable for relatively low throughput of the catalyst and less catalyst abrasion and is preferred here.

Between the regeneration and the reaction, it is in each case advisable to perform a flush step, preferably with nitrogen. In the case of regeneration, higher temperatures of 100 to 800° C., preferably 200 to 700° C., especially 300 to 550° C., are employed. These need not correspond to the reactor temperature during the glycerol conversion. In that case, corresponding heating and cooling steps are required. For the regeneration of the catalyst, preference is given to employing a higher temperature than in the reaction. The pressure in the regeneration is preferably between 0 and 50 bar, especially between 0 and 3 bar.

To regenerate the catalyst, at least one additive is used. This is preferably gaseous. When regeneration is effected under oxidizing conditions, it is a gaseous oxidizing agent. Preference is given to using air or oxygen. Carbon dioxide or other oxidizing agents may also be used. In addition, water or steam may be added. When regeneration is effected by hydrogenation, it is a gaseous reducing agent. In that case, preference is given to using hydrogen. To avoid high excess temperature in the catalyst zone as a result of the exothermic removal of the coke, the reducing gas is preferably used in diluted form, for which, for example, nitrogen or steam is used. During the regeneration of the catalyst, the concentration of the additive is preferably increased stepwise. The catalyst may be diluted by solid inert material or else be arranged in different zones.

It is also possible to use a mixture of oxidizing agent and reducing agent for the regeneration. In this case, however, one of the regenerating agents used is preferably present in excess compared to the other.

The desired catalytic properties and/or the acid function of the catalyst does not disappear through use of tungsten and promoters by the regeneration, as observed, for example, in the case of the classical acids, such as phosphoric acid or hydrochloric acid, which leads in turn to catalyst deactivation.

EXAMPLES

Comparative Example 1

A catalyst according to Patent Specification DE 4238493 (which is incorporated herein by reference) was used: 100 g of silicon oxide support having a diameter of about 4 mm were mixed with 25 g of 20% by weight phosphoric acid for 1 h. On a rotary evaporator, the excess water was then removed at approx. 70° C. 18 ml of this catalyst were introduced into a fixed bed reactor with a diameter of 15 mm. The reaction was then heated to a temperature of 250° C. By means of a pump, 12.5 g/h of a 20% by weight aqueous glycerol solution were passed into the reactor through an evaporator heated to 260° C. By means of gas chromatography, the stream was analysed at the reactor outlet. Up to an operating time of about 15 h, full conversion of glycerol could be observed. The selectivity and thus the yield were 79%. After approx. 15 h, the conversion and hence the yield fell steeply, such that only a conversion of 20% was present after 23 h. After the catalyst had been flowed through exclusively by a hydrogen stream of 4 l (STP)/h at a temperature of 350° C. for 5 h, no improvement in the yield (regeneration) could be detected. After the catalyst had been flowed through exclusively with an air stream of 4 l (STP)/h at a temperature of 350° C. for 5 h, a further deterioration in the yield was even detected.

Comparative Example 2

Comparative Example 1 was repeated, except that molybdic acid pressed to tablets was used as the catalyst. At a reactor temperature of 250° C., a yield of 9% was achieved within the first 5 h. Regeneration was dispensed with.

Example 1

Comparative Example 1 was repeated, except that tungstic acid pressed to tablets was used as the catalyst. At a reactor temperature of 260° C., a full conversion and a yield of 79% were achieved within the first 5 h. Within the next operating hours, the conversion and, correspondingly, the yield were reduced significantly. In the further course, a decline in the yield by approx. 5% per 10 h was detected. After the catalyst had been flowed through exclusively with a hydrogen stream of 4 l (STP)/h at a temperature of 350° C. for 10 h, the activity of the catalyst was improved significantly. The glycerol conversion was again complete at the start. In the further course, the conversion and the yield were reduced as before the regeneration. This cyclic operation of glycerol dehydration and regeneration of the catalyst was repeated three times within 300 h. After the unregenerated catalyst had been deinstalled, it was black in colour. The carbon content of the catalyst was 22% by weight, which indicates considerable carbonization.

Example 2

Comparative Example 1 was repeated, except that tungstic acid pressed to tablets was used as the catalyst. This catalyst was additionally impregnated with 1% by weight of Pd. To this end, lead acetate was used by means of incipient wetness. At a reactor temperature of 260° C., a full conversion and a yield of 77% were achieved within the first 5 h. Within the next operating hours, the conversion and, correspondingly, the yield were reduced significantly. After the catalyst had been flowed through exclusively with a hydrogen stream of 4 l (STP)/h at a temperature of 350° C. for 10 h, the activity of the catalyst was improved significantly. The glycerol conversion was then complete again at the start. Compared to Example 1, the decline in the conversion in the dehydration reaction was significantly lower after the regeneration, and the high conversion level was maintained for longer.

Example 3

Comparative Example 1 was repeated, except that a powder mixture of 15% by weight of montmorillonite and 85% by weight of $WO_3/ZrO_2$ (11% by weight of $WO_3$ on $ZrO_2$) pressed to tablets was used as the catalyst. At a reactor temperature of 260° C., a full conversion and a yield of 79% were achieved within the first 5 h. Within the next operating hours, the conversion and, correspondingly, the yield were reduced. After the catalyst had been flowed through exclusively with an air stream of 4 l (STP)/h at a temperature of 300° C. for 5 h, the activity of the catalyst was improved significantly. During the first hour of the regeneration, the air was diluted 1:1 with nitrogen in order to limit the exothermicity as a result of the burning-off of the coke. The glycerol conversion was again complete at the start after the regeneration. After 6 cycles of dehydration and of regeneration had been passed through, the regeneration temperature was increased to 390° C. In the subsequent dehydration, this led to a significantly enhanced conversion profile, where the glycerol conversion was still more than 90% after approx. 20 h.

Further variations and modifications of the invention will be apparent to those skilled in the art and are intended to be encompassed by the claims appended hereto.

The invention claimed is:

1. A process for regenerating a solid-state catalyst which comprises tungsten and having a Hammett acidity $H_o$ of <+2 and includes at least one promoter compound selected from the group consisting of a compound of gold, silver, copper, vanadium, platinum, palladium, rhodium, ruthenium, samarium, cerium, yttrium, scandium, lanthanum, zinc, magnesium, iron, cobalt, nickel and mixtures thereof, and optionally an additional compound of a element selected from the group consisting of lithium, sodium, potassium or cesium, and mixtures thereof and/or montmorillonite or an acidic zeolite, which catalyst, after use in a process for dehydrating glycerol to acrolein, has a lower activity and/or selectivity than before said dehydrating;

in which the process the catalyst is exposed to an oxidizing or reducing atmosphere for regeneration.

2. The process according to claim 1, in which a catalyst having a Hammett acidity $H_o$ of <+2 to −20 is regenerated.

3. The process according to claim 1, wherein the catalyst subjected to regenerating is a tungsten-containing compound selected from the group consisting of ammonium tungstate, tungstophosphoric acid, tungstic acid, tungstosilic acid, and a heteropolyacid with tungsten.

4. The process according to claim 1, in which the catalyst further comprises a natural or synthetic, silicatic or oxidic compound.

5. The process according to claim 1, in which the catalyst further comprises a support material modified with a mono- or di- or polybasic inorganic acid or salt of an inorganic acid.

6. The process according to claim 1, in which the catalyst further comprises, as a support material, aluminium oxide, titanium dioxide, silicon dioxide, zirconium dioxide, activated carbon or mixtures thereof.

7. The process according to claim 1, in which the promoter is selected from the group consisting of gold, silver, copper, vanadium and platinum, in the form of a compound thereof or in metallic form and the regenerating is carried out under oxidizing conditions.

8. The process according to claim 1, in which the promoter is selected from the group consisting of cobalt, nickel, palladium, rhodium and platinum, in the form of a compound thereof or in metallic form and the regenerating is carried out under reducing conditions.

9. The process according to claim 1, in which regeneration time for the catalyst between dehydrating of the glycerol is less than 24 h.

10. The process according to claim 1, in which reaction time for dehydrating of glycerol of the catalyst is more than 10 h.

11. The process according to claim 1, in which regeneration temperature of the catalyst is between 260 and 550° C.

12. The process according to claim 1, in which a regenerating agent is used which is air.

13. The process according to claim 1, in which a regenerating agent is used which is hydrogen.

14. The process according to claim 1, in which regeneration is performed in a fixed bed reactor, in a fluidized bed reactor, in a reactor with a circulating fluidized bed, in a moving bed reactor or in a reactor with regenerator-riser (-downer) design.

* * * * *